United States Patent [19]

Maeda

[11] Patent Number: 4,737,027
[45] Date of Patent: Apr. 12, 1988

[54] OPTICAL FIBER MEASURING APPARATUS

[75] Inventor: Minoru Maeda, Tokyo, Japan

[73] Assignee: Ando Electric Co., Ltd., Tokyo, Japan

[21] Appl. No.: 42,408

[22] Filed: Apr. 24, 1987

[30] Foreign Application Priority Data

Apr. 24, 1986 [JP] Japan .................................. 61-95726

[51] Int. Cl.[4] ......................... G01N 21/84; G02F 1/33
[52] U.S. Cl. .................................... 356/73.1; 350/358
[58] Field of Search ....................... 356/73.1; 350/358

[56] References Cited

FOREIGN PATENT DOCUMENTS 58-106526 6/1983 Japan .................................... 350/358

Primary Examiner—Vincent P. McGraw
Attorney, Agent, or Firm—Seidel, Gonda, Goldhammer & Abbott

[57] ABSTRACT

An optical fiber measuring apparatus comprises a first laser diode and a second laser diode for producing light outputs of different wavelengths, respectively, a polarized beam splitter to which the light output of the first or second diodes is inputted, an A/O modulator through which the light output having passed through the polarized beam splitter is supplied to an optical fiber, and a first change-over switch for changing over power supplies for the first and second laser diodes, and first and second driving sources for driving the A/O modulator. The outputs of the drive sources are selectively changed over by a second change-over switch. The first and second change-over switches are interlocked in such a manner in which the output of the first driving source is selected when said first power supply is turned on while the output of the second driving source is selected when the output of the second power supply is turned on. The output frequencies of the first and second driving sources are so selected that the light output from the A/O modulator exhibits same first order diffraction angle for the output wavelengths of the first and second laser diodes.

1 Claim, 1 Drawing Sheet

OPTICAL FIBER MEASURING APPARATUS

BACKGROUND OF THE INVENTION

1. Field of the Invention

The present invention relates to an apparatus for measuring characteristics of optical fibers by employing a plurality of light sources.

2. Description of the Prior Art

In the optical fiber measuring apparatus of this type, inputting/outputting of light beams emitted by laser diodes constituting the light sources as well as echo light beams from an optical fiber due to the back scattering or the like phenomena in correspondence to the laser light beams must be processed by a single optical connector. Consequently, various types of optical switches and optical couplers/decouplers are required.

As the optical switch, there is universally employed an acoustooptical device (hereinafter referred to as A/O modulator) in view of insignificant polarization characteristics and the capability of high-degree isolation between the signals to be processed.

At present, for the measurement of the optical fibers, there are made use of two wavelengths of 1.3 $\mu$m and 1.55 $\mu$m as light sources. To this end, there must be provided two light sources of the different wavelengths mentioned above and light-beam change-over switches.

Further, for the measurement of the characteristics of optical fibers, the measuring instrument or apparatus has to be frequently transported. Accordingly, there exits a need for the apparatus of small size and light weight. When these various components or devices can be housed within a single casing so as to be controlled through operation of switches installed on a control panel of the casing, the measurement can be carried out effectively.

SUMMARY OF THE INVENTION

It is therefore an object of the present invention to provide an optical fiber measuring apparatus which can enjoy a high-speed operation and a high reliability.

According to an aspect of the invention, the above object can be accomplished by changing over light sources of different wavelengths by means of a change-over switch and using a polarized light beam splitter of low insertion loss while driving the A/O modulator by changing over the associated driving sources in correspondence with the wavelengths of the light sources.

BRIEF DESCRIPTION OF THE DRAWING

The FIG. 1 shows schematically a general arrangement of an optical fiber measuring apparatus according to an embodiment of the invention.

DESCRIPTION OF THE PREFERRED EMBODIMENTS

Figure 1:
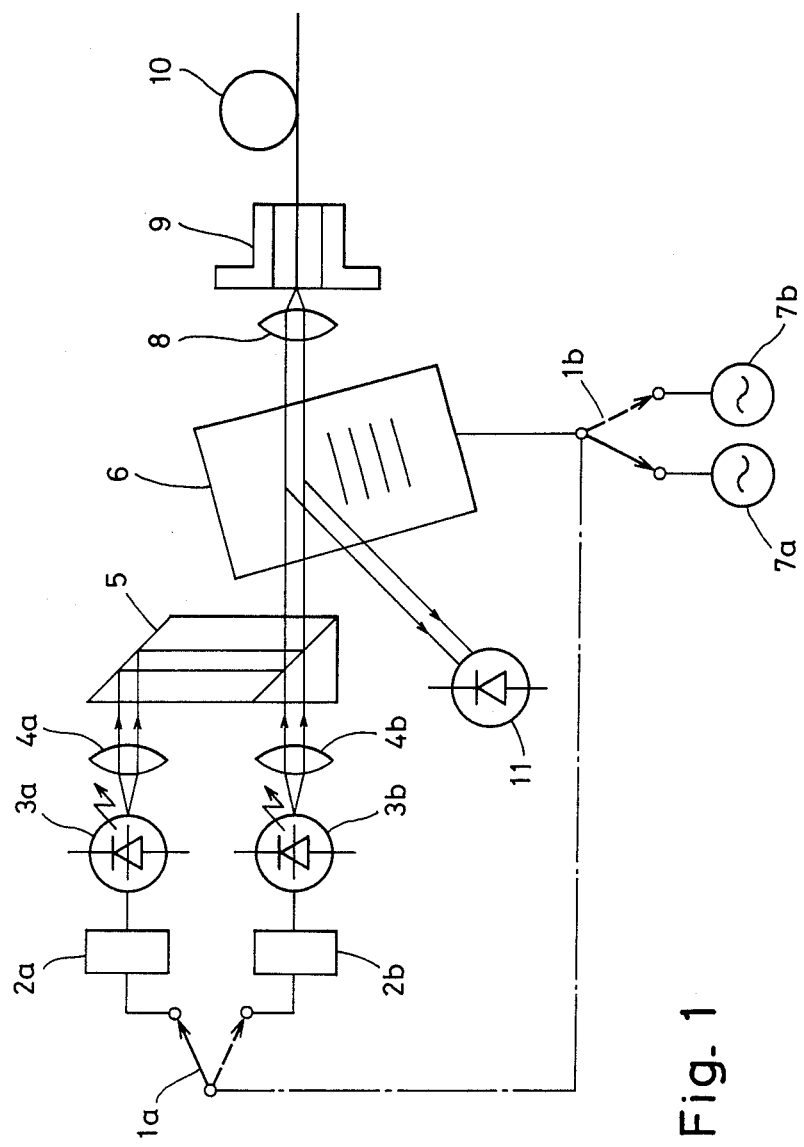

Now, the present invention will be described in detail in conjunction with an exemplary embodiment by reference to FIG. 1.

In FIG. 1, reference symbols 1a and 1b denote change-over switches, respectively, 2a and 2b denote power supply sources, respectively, 3a denotes a laser diode of 1.3 $\mu$m in wavelength, 3b denotes a laser diode of 1.55 $\mu$m in wavelength, 4a and 4b denote condenser lenses, respectively, 5 denotes a polarized beam splitter, 6 denotes an A/O modulator, 7a and 7b denote drive sources, respectively, 8 denotes a condenser lens, 9 denotes an optical connector, 10 denotes an optical fiber, and finally a reference numeral 11 denotes a photodetector.

In operation, light rays emitted by the laser diode 3a are collimated by means of the condenser lens 4a to be converted to a S-polarized light beam.

Similarly, light rays emitted by the laser diode 3b are collimated by means of the condenser lens 4a to be converted to a P-polarized light beam.

Both the collimated light beams from the lenses 4a and 4b are inputted to the polarized beam splitter 5 and revolved on a plane intersecting perpendicularly the optical axis to give S- and P-polarized light beams, respectively, to be subsequently transmitted through the A/O modulator 6, the output light beam of which is then collected by the condenser lens 8 to be supplied to the optical fiber 10 as the measuring light beam through the optical connector 9.

The driving sources 7a and 7b are each constituted by a signal generator for driving the A/O modulator 6, wherein the output frequencies of the driving sources 7a and 7b are so selected that the first order diffraction angle of the light beam having the wavelength of 1.3 $\mu$m may coincide with that of the light beam of 1.55 $\mu$m in wavelength. In this connection, it is to be noted that the first order diffraction angle $\theta$ is defined by the following expression:

$$\theta = \lambda f / 2nv \qquad (1)$$

where $\lambda$ represents the wavelength of incident light, f represents the frequency of the driving signal, n represents the refractive index of the element constituting te A/O modulator 6, and v represents the sound velocity within the A/O modulator element 6.

The change-over switch 1a is so arranged as to change over the power supply source 2a for the laser diode 3a and the power supply source 2b for the laser diode 3b with each other, while the change-over switch 1b is interlocked with the change-over switch 1a so as to exchange the driving sources 7a and 7b with each other.

Thus, when the power supply source 2a for the laser diode 3a is turned on by the change-over switch 1a, the change-over switch 1b selects the output frequency of the driving source 7a to be supplied to the A/O modulator 6. On the other hand, when the power source 2a for the laser diode 3b is turned on by the change-over switch 1a, the change-over swiotch 1b selects the output frequency of the driving source 7b to be supplied to the A/O modulator 6.

Upon appearance of echo light from the optical fiber 10 due to the back scattering, the echo light is diffractd by the A/O modulator 6 to be subsequently detected by the photodetector 11. In this manner, the characteristics of the optical fiber 10 can be measured.

As will be appreciated from the foregoing description, the present invention has now provided such an arrangement in which the outputs of the laser diodes having different wavelengths are supplied to the optical fiber by way of the polarized beam splitter and the A/O modulator, wherein the output light beams of the laser diodes are changed over simultaneously with the exchange of the driving frequencies. By virtue of this arrangement, there can be realized a measuring apparatus of small size and light weight, which can also enjoy low insertion loss.

I claim:

1. An optical fiber measuring apparatus, comprising:

a first laser diode and a second laser diode for producing light outputs of mutually different frequencies;

a polarized beam splitter to which the light output of said first or second diodes is inputted;

an A/O modulator through which the light output having passed through said polarized beam splitter is supplied to an optical fiber;

a first change-over switch for changing over power supplies for said first and second laser diodes;

first and second driving sources for driving said A/O modulator, said driving sources being selectively changed over by a second change-over switch, said first and second change-over switches being interlocked in such a manner in which the output of said first driving source is selected when said first power supply is turned on while the output of said second driving source is selected when the output of said second power supply is turned on;

wherein the output frequencies of said first and second driving sources are so selected that the light output from said A/O modulator exhibits same first order diffraction angle for the output wavelengths of said first and second laser diodes.

* * * * *